*United States Patent* [19]

Sheehan

[11] Patent Number: 5,582,696

[45] Date of Patent: Dec. 10, 1996

[54] GLUCOSE LEVEL MONITORING APPARATUS

[75] Inventor: Timothy P. Sheehan, Altadena, Calif.

[73] Assignee: Health Craft International, Inc., Pasadena, Calif.

[21] Appl. No.: 252,551

[22] Filed: May 31, 1994

[51] Int. Cl.[6] .......................... G01N 27/06; G01N 27/26
[52] U.S. Cl. ...................... 204/403; 204/415; 422/82.01;
422/82.02; 422/68.1; 436/95; 435/817;
435/286.1; 435/287.8; 435/287.9
[58] Field of Search .................................. 204/403, 409,
204/418, 415; 422/82.01, 82.02, 68.1; 436/95;
435/288, 817

[56] References Cited

U.S. PATENT DOCUMENTS

| | | |
|---|---|---|
| 3,994,594 | 11/1976 | Sandrock et al. .................... 422/102 X |
| 4,303,076 | 12/1981 | Danek ..................................... 128/635 |
| 4,539,855 | 9/1985 | Jacobs ................................... 422/100 X |
| 4,654,127 | 3/1987 | Baker et al. ...................... 422/82.02 X |
| 4,757,022 | 7/1988 | Shults et al. ............................. 435/291 |
| 4,847,050 | 7/1989 | Jenkins et al. ......................... 422/102 |
| 4,929,426 | 5/1990 | Bodai et al. ...................... 422/82.02 X |
| 4,933,066 | 6/1990 | Osaka et al. ............................ 204/403 |
| 4,935,106 | 6/1990 | Liston et al. .......................... 204/153.1 |
| 5,056,521 | 10/1991 | Parson et al. .......................... 128/635 |
| 5,114,859 | 5/1992 | Kagenow ......................... 422/82.01 X |
| 5,228,972 | 7/1993 | Osaka et al. ............................ 204/415 |
| 5,269,891 | 12/1993 | Colin ...................................... 204/403 |

*Primary Examiner*—Arlen Soderquist
*Attorney, Agent, or Firm*—Christie, Parker & Hale, LLP

[57] ABSTRACT

A seal and wiper assembly covers the opening of a reservoir of buffer solution in a blood glucose level. A monitor. A replaceable test cap is designed for single use. As the test cap is installed, a clock starts to run. After a predetermined time, the clock disables the monitor. As the test cap is removed from the buffer, the assembly wipes the buffer from the glucose sensor.

3 Claims, 7 Drawing Sheets

GLUCOSE LEVEL MONITORING APPARATUS

FIELD OF THE INVENTION

This invention relates to the field of medical testing and, more particularly, to a method and apparatus for measuring human glucose levels.

BACKGROUND OF THE INVENTION

For a number of years, polarographic systems with an enzyme electrode have been used to measure glucose levels in blood samples. For example, Clark U.S. Pat. No. 3,539,455 teaches the use of a platinum anode and silver cathode to measure the hydrogen peroxide produced by the reaction of glucose and oxygen in the presence of a glucose oxidase enzyme. Newman U.S. Pat. No. 3,979,274 discloses a laminated membrane for an enzyme electrode in which the enzyme is coupled with an adhesive between the lamina. The lamina of the multi-ply membrane comprise an outer support layer that serves as a barrier to high molecular weight substances and an inner homogeneous layer that serves as a barrier to interfering low molecular weight materials, but permits hydrogen peroxide to pass through, and an intermediate enzyme layer that reacts with glucose and bonds the outer and inner layers together. Glucose passes through the outer layer and reacts with a surplus of oxygen in the presence of the contained enzyme. Hydrogen peroxide, which is one of the reaction products, passes through the inner layer to the electrode. The resulting electric current is a measure of the level of glucose in the sample fluid under test.

SUMMARY OF THE INVENTION

A portable, hand-held testing device, using electrode and membrane technology, combining to form a sensor, from laboratory analyzers, has been developed. This monitor maintains the membrane and electrode under wet conditions between tests by a design that places the electrode and sensor in a fluid buffer reservoir between uses for testing.

A method has been devised to retain the buffer solution in the reservoir so a minimum is lost each time the membrane and electrode are removed from the reservoir for testing. The reusable test surface, the membrane, has a finite life which is a combination of the number of readings of the electrode and the number of days the membrane is in use. A plastic structure has been built which contains the membrane. This test cap is built to snap-lock in place, positioning the membrane properly over the electrode, and to break apart upon removal from the electrode pedestal. The test cap destruction assures it will not be reused in testing beyond its controlled life.

A small sample of blood is placed on a multi layer membrane positioned on an electro chemical electrode. The multi layer membrane contains an enzyme particular to the type of test (e.g. glucose, lactate, etc.). Between tests the membrane must be washed or flushed, maintained wet, and provided with oxygen which is depleted during testing. A hand held test monitor case contains a replaceable liquid buffer reservoir and an electro chemical electrode mounted on the underside of a lid so when the lid is opened, the sensor tip is rotated to the open position, the sensor sits perpendicular to the top surface of the monitor case and is ready to receive a blood test sample. A plastic structure, the test cap, fits on the electrode pedestal and positions the membrane over the electrode tip in a particular, stretch fit. A top orifice in the reservoir permits the sensor tip to enter the reservoir. A seal and wiping assembly across this orifice prevents buffer spillage when the monitor lid is opened or closed. The seal and wiping assembly also remove excess buffer from the sensor and test cap surfaces as they emerge from the reservoir. A triangular shaped fossa in the test cap receives and holds the excess buffer from the wiping action. Three perpendicular grooves in the side of the electrode pedestal guide installation of the test cap which has three perpendicular tabs which fit into the pedestal grooves and snap-lock into a notch at the proximal end of each groove on the electrode pedestal, properly positioning the test cap membrane on the electrode tip and stretches the membrane to the proper tension. Upon test cap installation, a sensor switch in the monitor lid, under the test cap and adjacent to the base of the sensor pedestal, is activated by contact with the base of the test cap. This connection resets the monitor's timing system which tracks the number of days of test cap use. Test caps are replaced by rotating or twisting which breaks the plastic tabs and permits removal from the electrode pedestal. Breaking the tabs prevents test cap reuse since the tab guides and the snap-lock mechanism are destroyed. The replaceable buffer reservoir snap fits into the monitor case, preventing spillage and leakage by facilitating the seal with the monitor lid. A nipple on the test cap reservoir gasket seal forces the monitor lid upward upon opening, facilitating rotation of the lid so the full open position and activating a display warning if the lid is not fully closed after use.

According to one aspect of the invention, the monitor case buttons are depressed, the monitor lid is forced open by a nipple in the reservoir gasket under the lid, and the lid is rotated open and ready for testing. In this process, the elastic wiper assembly sealing the buffer reservoir orifice automatically wipes the test cap (containing the membrane and which has been slipped over the electrode pedestal), returning excess fluid buffer to the reservoir. Also, the final drop(s) of buffer, remaining on the membrane surface, are pushed into a fossa on the front of the test cap structure. The monitor lid is opened when the buttons are depressed, releasing the latches and thereby allowing expansion of a compressed nipple on the reservoir gasket to help force the monitor lid open. This permits an easier grip on the side of the lid as it is rotated into the fully open position.

According to another feature of the invention, a sample of blood is placed on the membrane surface by pricking a finger, allowing a few seconds for a small blood drop to form before placing the blood onto the reusable membrane test surface.

According to another feature of this invention, a test cap is removed after its useful life has expired. In the removal process, the test cap is rotated, breaking three internal test cap tabs which are used to align the test cap upon installation and which act to position the test cap snugly in place by snap-locking the tab barbs into notches in the electrode pedestal grooves.

According to another feature of the invention, the test cap tabs slide into three grooves in the sensor pedestal, aligning the test cap and membrane. When the test cap is moved onto the electrode pedestal and pushed down, the ends of the tabs, the barbs, snap-lock into notches in the grooves on the electrode pedestal, locking the test cap and membrane in position for testing.

According to another feature of the invention, the test cap contains a microswitch in the bottom side of the base that, when the test cap is installed, activates a switch in the monitor lid. This connection signals the monitor's electronics that a new test cap has been installed and the counter (of tests performed) and clock (of days of use) are reset.

According to another feature of the invention, the replaceable buffer reservoir snap fits into the monitor base so the reservoir does not slide and move apart from the monitor when both are moved or rotated into different positions. This prevents buffer solution spillage and insures the buffer reservoir is always properly placed. If the reservoir is not properly placed, the monitor lid will not close, resulting in warning messages on the monitor display.

BRIEF DESCRIPTIONS OF THE DRAWINGS

The features of specific embodiments of the best mode contemplated of carrying out the inventions are illustrated in the drawings, in which.

DETAILED DESCRIPTION OF THE SPECIFIC EMBODIMENT

The disclosure of application Ser. No. 08/103,425, filed on Aug. 8, 1993 is incorporated fully herein by reference. The present invention is an improvement of the glucose level monitoring apparatus disclosed in the referenced application.

Figure 1A:
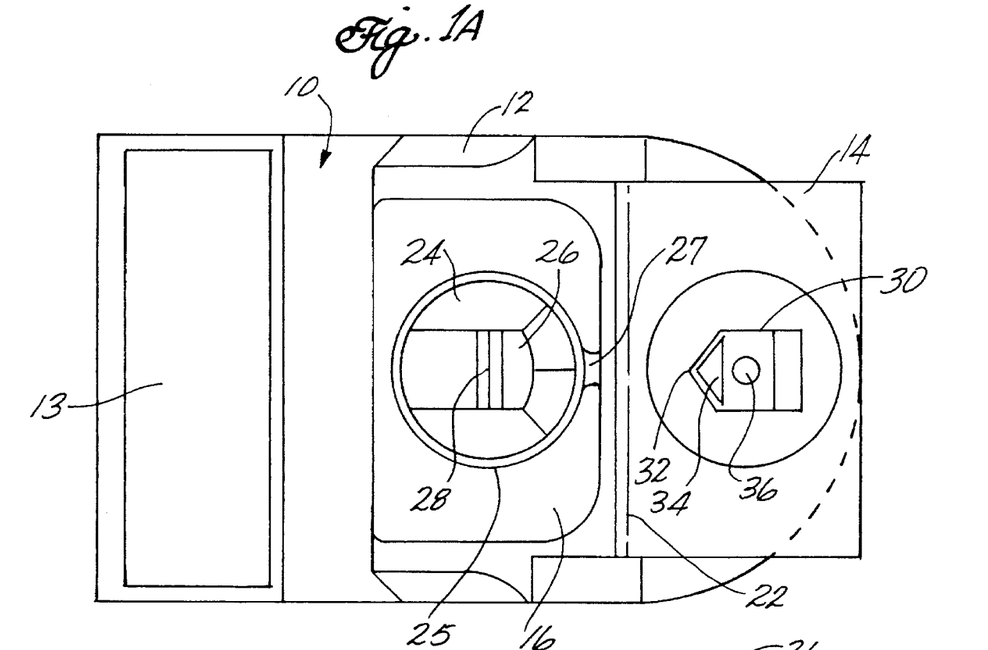
FIGS. 1A and 1B are top and side views of the monitor case, replaceable reservoir, and replaceable test cap.
Figure 1B:
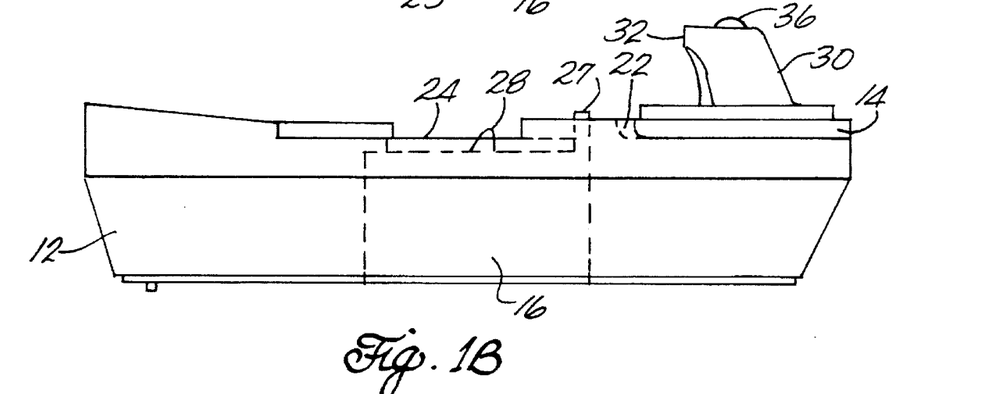
Figure 7:
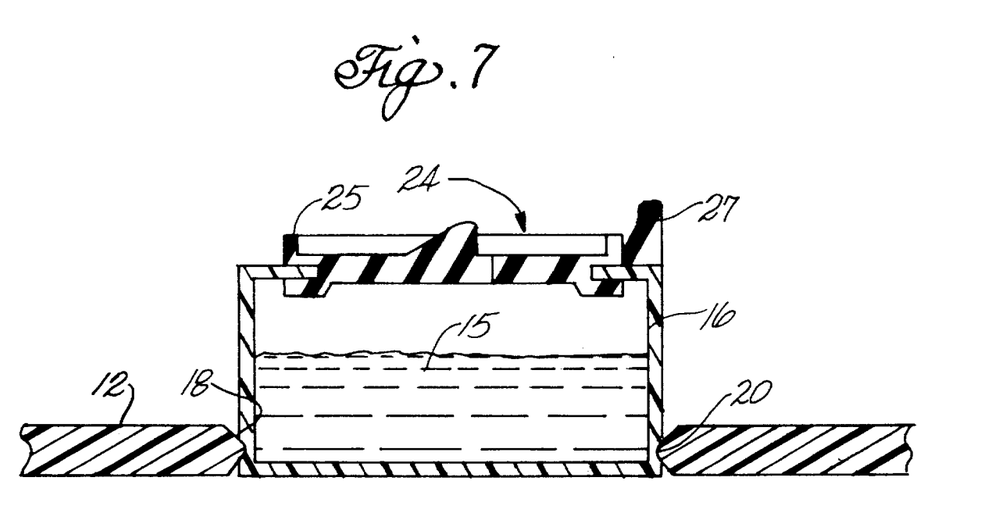
FIG. 7 is a detailed cross sectional view showing the snap fit feature of the replaceable buffer reservoir.

As shown in FIGS. 1A and 1B, a case 10 has a base 12, an electronic display 13, and a lid 14 hinged to base 12. A buffer solution 15 is stored in a replaceable reservoir 16 that fits into a cavity formed in base 12. Reservoir 16 is a six sided box having a circular opening in the top. Base 12 has a protrusion 18 and reservoir 16 has detents 20 that snap into protrusion 18 to secure reservoir 16 in place (FIG. 7). Lid 14 is attached to base 12 by a hinge 22 and has a latch (not shown) to secure lid 14 in its closed position. A seal and wiper assembly 24 covers the opening in the top of reservoir 16. Seal and wiper assembly 24 serves to prevent spillage and evaporation of buffer solution 15. Assembly 24 has an annular groove into which the top edge of reservoir 16 around the hole fits (FIG. 7) and has a flap 26 on which a ridge shaped squeegee 28 is formed. Assembly 24 is made in a molded one piece construction from a suitable elastic neoprene or plastic material.

Figure 2A:
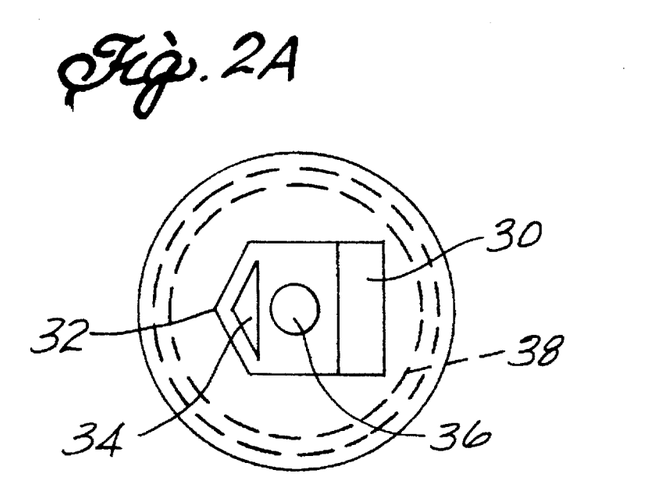
FIGS. 2A and 2B are top and side views of the replaceable test cap, the membrane surface, and the fluid-collecting fossa.
Figure 2B:
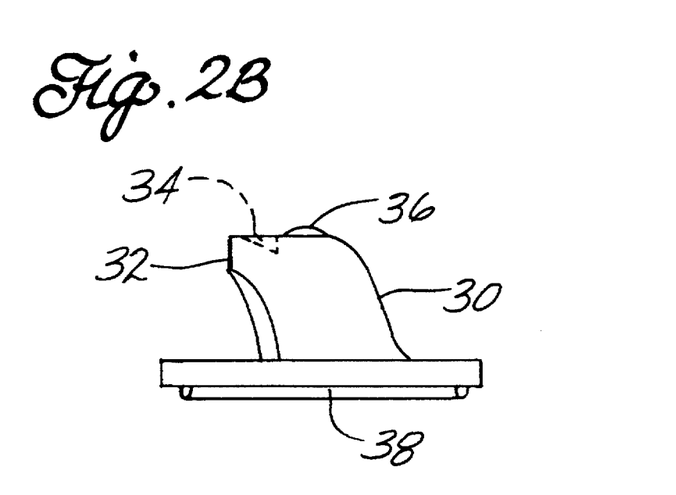

A membrane test cap 30 is replaceably mounted on lid 14 as described in greater detail below. As shown in FIGS. 2A and 2B, cap 30 has a knife edge 32 that faces reservoir 16 when lid 14 is opened and a fossa 34 to collect buffer solution as cap 30 is removed from reservoir 16. A membrane 36 is exposed on top of cap 30. The base of cap 30 has an annular ridge 38 that actuates a switch to start a clock in the electronics of the apparatus as described in more detail below.

Figure 3A:
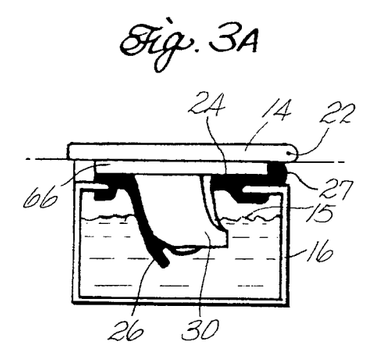
FIGS. 3A to 3D are detailed cross sectional and side views showing the wiping sequence as the monitor lid is opened.
Figure 3B:
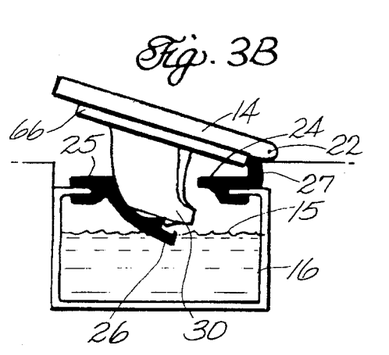
Figure 3C:
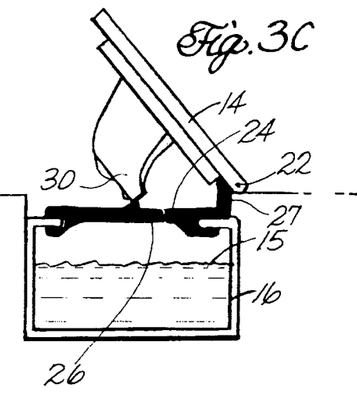
Figure 3D:
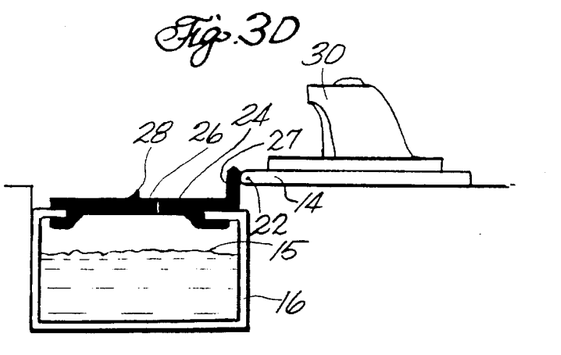

Seal wiper assembly 24 and membrane test cap 30 are designed to automatically wipe the surface of membrane 36 as lid 14 is opened so that membrane 30 does not have to be blotted by the user. This process is illustrated in FIGS. 3A to 3D. Although lid 14 and hinge 22 are illustrated in FIGS. 3A to 3D, base 12 is not shown. In FIG. 3A lid 14 is not shown and membrane 36 is submersed in buffer solution 15. Flap 26 is elastically deflected by and bears against the back surface of cap 30. As shown in FIG. 3B, as lid 14 begins to open, membrane 36 rises out of buffer solution 15 and flap 26 continues to bear against cap 30 as cap 30 rises. Squeegee 28 sweeps across the surface of membrane 36, thereby wiping buffer solution therefrom and pushing the buffer solution toward knife edge 32. As shown in FIG. 3C, as lid 14 is opened further, flap 26, returning to its rest condition, closes completely and squeegee 28 separates from knife edge 32 to remove any remaining residual droplets from cap 30. As shown in FIG. 3D, lid 14 is completely opened, membrane 36 faces upwardly, any residual buffer solution on the top surface of test cap 30 is collected in fossa 34.

Figure 4A:
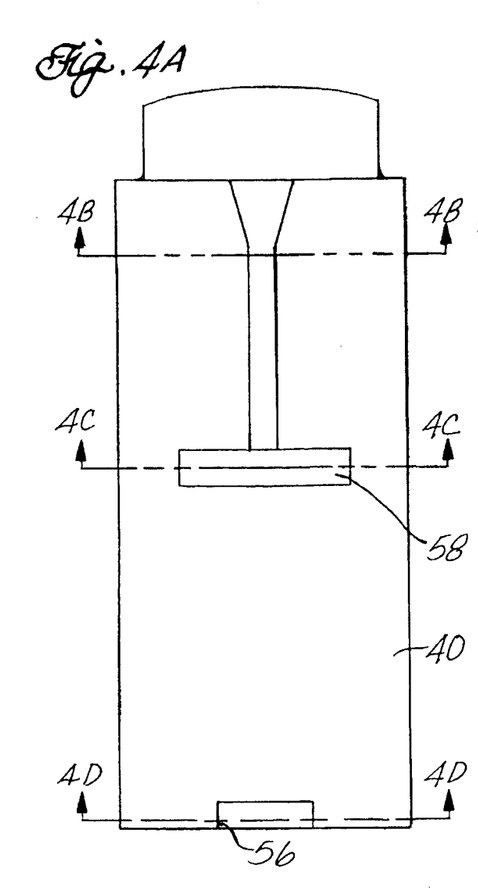
FIGS. 4A to 4D are elevation and cross sectional views of the electrode pedestal showing tab guide grooves.
Figure 4B:
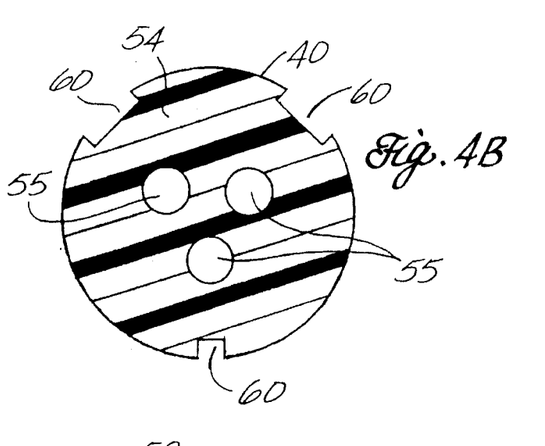
Figure 4C:
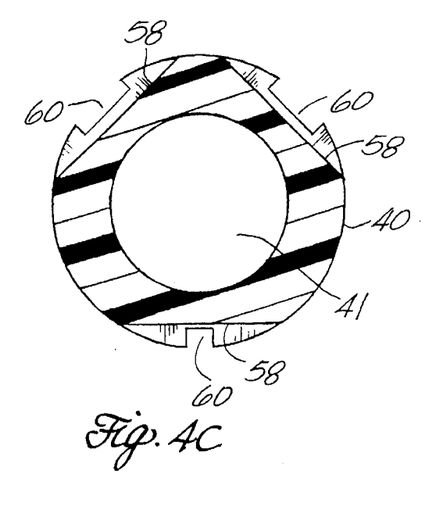
Figure 4D:
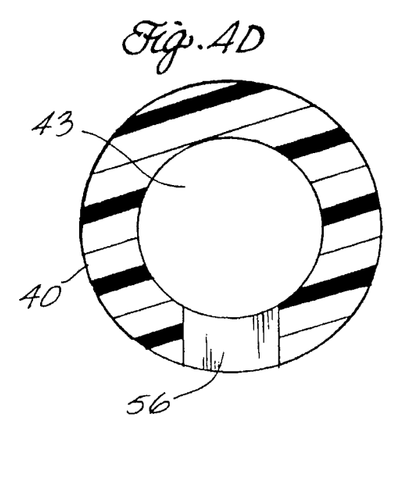
Figure 5:
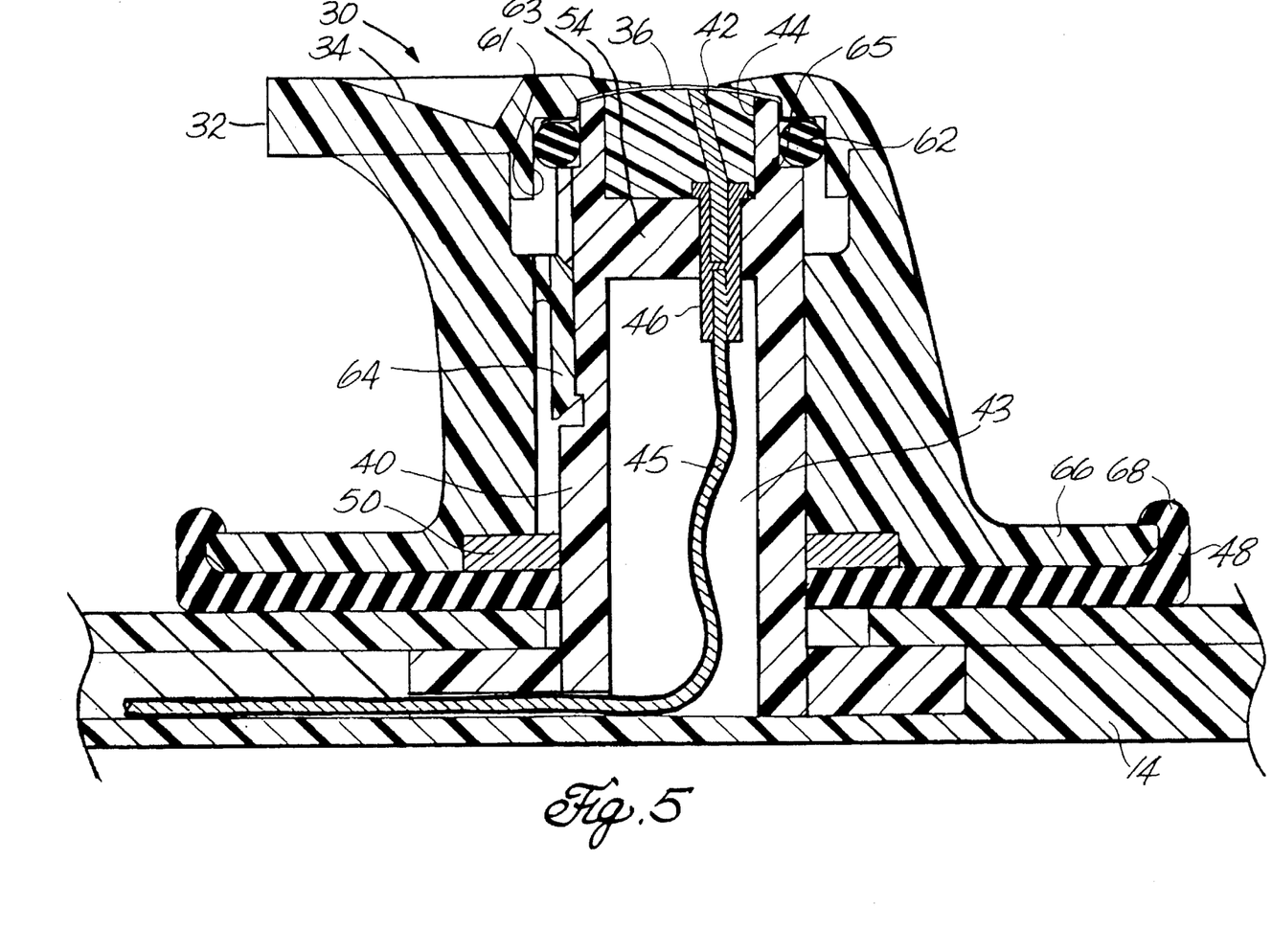
FIG. 5 is a cross sectional view of the test cap and sensor assembly showing the two guiding tabs and the electrode in the bottom base of the test cap snap-lock barb.

As shown in FIG. 5, test cap 30 fits on a hollow cylindrical electrode pedestal 40, which is mounted in lid 14. As shown in FIGS. 4A to 4D, Pedestal 40 is made of an electrical insulator and is divided by a horizontal partition 54 into an upper chamber 41 and a lower chamber 43. A dome-shaped electrode 42 is disposed in upper chamber 41. Electrode 42 comprises a plurality of electrodes (not shown), for example, as described in U.S. Pat. No. 3,979,274 the disclosure of which is incorporated fully herein by reference. Partition 54 has vertical holes 55 for receiving electrical connectors 46. Three electrical wires, one of which is illustrated at 44, lead from the electrodes of electrode 42 to respective electrical connectors 46. Three other electrical wires, one of which is illustrated at 45, lead from electrical connectors 46 through a bottom opening 56 in lower chamber 43 and lid 14 to the electronics housed in case 12. A rubber seal 48 for retaining test cap 30 is mounted on the surface of lid 14 around pedestal 40. Seal 48 is secured by a retaining ring 50.

Around the middle of pedestal 40, a plurality (e.g., three in number) of horizontal flats 58 are formed in the cylindrical outer surface of pedestal 40. A plurality (e.g., three in number) of slots 60 extend from the top of pedestal 40 downwardly in a vertical direction to flats 58. As depicted in FIG. 4C, the depth of slots 60 is designed so the centers of flats 58 are closer to the center axis of pedestal 40 than the base of slots 60 so that flats 58 can perform the test cap snap-locking function described below.

As previously stated test cap 30 is removably mounted on pedestal 40. The top of test cap 30 has a cavity 61 that matches the curvature of electrode 42 and a bezel 63 that defines an opening through which membrane 36 is exposed. Membrane 36 is retained inside cavity 61 by an O-ring seal 62. Seal 62 is slightly compressed by the top and sides of cavity 61. Pedestal 40 has an annular shoulder 65 around chamber 41. The top of pedestal 40 fits into cavity 61 such that shoulder 65 bears against and compresses seal 62 and the end of electrode 42 bears against and tensions membrane 36. Cap 30 has a plurality (e.g., three in number) of hook ended snap lock barbs 64 that are designed to fit in slots 60. The spacing between two of slots 60 is slightly less than the spacing between them and the third slot. The same is true as to the spacing between flats 58. Barbs 64 are spaced apart the same distance as slots 60 so that they fit in slots 60 in only one angular orientation. As a result, test cap 30 can only be mounted on pedestal 40 in one specific orientation. The bottom of cap 30 has an outwardly flared flange 66 that is engaged by an inwardly oriented lip 68 on seal 48. The height of cap 30 is designed relative to pedestal 40 so that when cap 30 is seated on pedestal 40 with the hooks of barbs 64 engaging the top edge of flats 58, seal 62 is compressed and membrane 36 is stretched across the surface of electrode 42. Thus, uniform tension can be maintained on membrane 36 each time test cap 30 is replaced. Barbs 64 are preferably designed so they must be broken in order to remove cap 30 from pedestal 40. As a result, cap 30 cannot be reused. This provides assurance that membrane will not be used beyond its designed life.

Figure 6A:
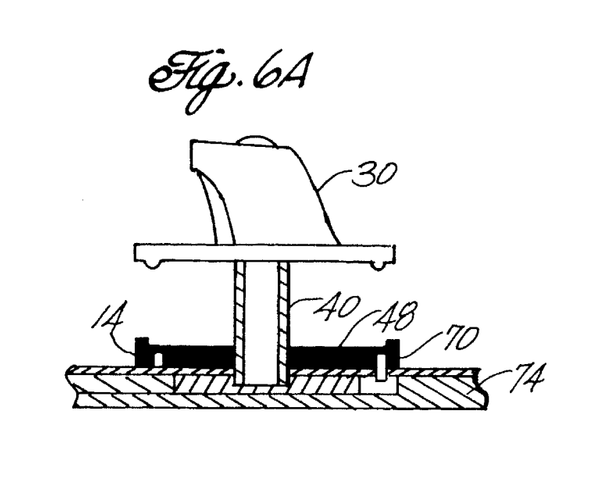
FIGS. 6A and 6B are cross sectional and side views showing the test cap activation switch to control a clock which determines the test cap usage life.
Figure 6B:
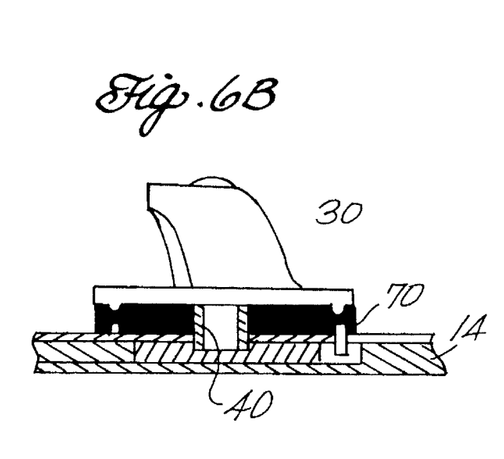

As illustrated in FIGS. 6A and 6B, a microswitch 70 is mounted under seal 48. When a new test cap 30 is installed on pedestal 40, the force exerted on switch 70 during installation actuates switch 70 and starts a clock in the electronics section of the apparatus. A counter in the electronics counts the number of times lid 14 is opened, which is representative of the number of reading made with the sensor. After a predetermined combination of the number of readings of the sensor as measured by the counter and the number of days the membrane is in use as measured by the clock, display 13 is disabled so that the apparatus cannot be used any longer. When test cap 30 is removed and switch 70 is turned off, the counter and the clock in the electronics are reset. The timing cycle then repeats after a new test cap is installed on pedestal 40. The described snap-locking arrangement and electronics insures that the apparatus will be used in accordance with prescribed conditions of replacement of the membrane.

As shown in FIG. 7, assembly 24 has an annular outer gasket surface 25 that seals against and is compressed by the annular surface of flange 66 when lid 14 is closed (FIGS. 1A and 3A). Thus, reservoir 16 is sealed by flange 66 when lid 14 is closed and is sealed by flap 26 when lid 14 is open. Reservoir 16 is only unsealed while it is being opened.

Assembly 24 also has a resilient, upwardly extending nub 27 that is compressed when lid 14 is closed to urge lid 14 into an unlatched position. (Compare FIGS. 3A to 3D.) Therefore, if lid 14 is inadvertently not properly latched or becomes unlatched, the lid is popped upwardly by the return force of nub 27 into an obviously open position so the user is warned of this condition.

The described embodiment of the invention is only considered to be preferred and illustrative of the inventive concept; the scope of the invention is not to be restricted to such embodiments. Various and numerous other arrangements may be devised by one skilled in the art without departing from the spirit and scope of this invention.

What is claimed is:

1. Apparatus for monitoring glucose level comprising:

a case having a base member and a lid member adapted to cover and uncover the base member;

a reservoir having an opening disposed in the base member;

a polarographic membrane cell and glucose level sensing electrode mounted in the lid member such that the membrane passes through the opening into the reservoir when the lid member covers the base member, the cell and electrode forming in the lid member a test cap that has sides and a top in which the membrane is mounted;

a buffer solution disposed in the reservoir to wet the membrane when the lid covers the reservoir;

means for covering the opening when the lid uncovers the reservoir and uncovering the opening when the lid covers the base member, the covering and uncovering means comprising a seal and wiper assembly on the base member having a flap through which the test cap passes when the lid covers the base member and an elastic gasket that surrounds the test cap on the lid to seal the opening when the lid covers the base member;

the seal and wiper assembly covering the opening of the reservoir in a manner to wipe the sides of the test cap as the test cap is removed from the buffer reservoir prior to monitoring glucose level and to retain the buffer solution in the reservoir and maintain the buffer solution level such that, as the test cap continues to be rotated out of the reservoir, the seal and wiper assembly wipes excess buffer solution from the membrane mounted in the top of the test cap, retaining that buffer solution in the reservoir, and the portion of the test cap adjacent to the membrane in the top of the test cap forms a fossa for the final drop of buffer solution wiped by the elastic wiper assembly; and means connected to the electrode for displaying glucose level.

2. The apparatus of claim 1, in which the cell and electrode form a test cap that cannot be reused after removal from the other member, the apparatus comprising:

a pedestal adapted to receive the test cap;

perpendicular grooves cut into the pedestal to act as guides;

barbs formed in the test cap being slidable into the grooves, each barb terminating with a small hook end which snaps into a depression in the groove, firmly positioning the test cap into place;

the test cap being removable by rotating which breaks the barbs releasing the test cap and rendering the test cap unusable.

3. The apparatus of claim 1, in which the test cap has a ridge along the under-surface that activates a switch as the test cap is installed, the apparatus additionally comprising a calendar clock and counter which are reset and activated by the switch.

* * * * *

UNITED STATES PATENT AND TRADEMARK OFFICE
CERTIFICATE OF CORRECTION

PATENT NO. : 5,582,696
DATED :
INVENTOR(S) : December 10, 1996

Timothy P. Sheahan

It is certified that error appears in the above-indentified patent and that said Letters Patent is hereby corrected as shown below:

On the title page, item [75] Inventor: "Timothy P. Sheehan" should read --Timothy P. Sheahan--.

Signed and Sealed this

Fourteenth Day of October, 1997

*Attest:*

BRUCE LEHMAN

*Attesting Officer*  *Commissioner of Patents and Trademarks*